US007285670B2

(12) United States Patent
Chorghade et al.

(10) Patent No.: US 7,285,670 B2
(45) Date of Patent: *Oct. 23, 2007

(54) SYNTHESIS OF SUBSTITUTED THIAZOLINE CARBOXYLIC ACIDS

(75) Inventors: Mukund S. Chorghade, Natick, MA (US); Rayomand H. Gimi, Chelmsford, MA (US); Peter D. McDonnell, Edmunds (GB); Paul Wolstenholme-Hogg, Haverhill (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/242,640

(22) Filed: Oct. 3, 2005

(65) Prior Publication Data

US 2006/0217561 A1 Sep. 28, 2006

Related U.S. Application Data

(63) Continuation of application No. 10/439,263, filed on May 15, 2003, now Pat. No. 6,982,335.

(60) Provisional application No. 60/392,833, filed on Jun. 27, 2002, provisional application No. 60/381,012, filed on May 15, 2002, provisional application No. 60/381,021, filed on May 15, 2002, provisional application No. 60/380,894, filed on May 15, 2002, provisional application No. 60/380,910, filed on May 15, 2002, provisional application No. 60/380,880, filed on May 15, 2002, provisional application No. 60/381,017, filed on May 15, 2002, provisional application No. 60/380,895, filed on May 15, 2002, provisional application No. 60/380,903, filed on May 15, 2002, provisional application No. 60/381,013, filed on May 15, 2002, provisional application No. 60/380,878, filed on May 15, 2002, provisional application No. 60/380,909, filed on May 15, 2002.

(51) Int. Cl.
*C07D 277/14* (2006.01)

(52) U.S. Cl. ...................... 548/200; 548/201

(58) Field of Classification Search ............... 548/200, 548/201

See application file for complete search history.

(56) References Cited

U.S. PATENT DOCUMENTS

| | | | |
|---|---|---|---|
| 4,406,905 A | 9/1983 | Zähner et al. |
| 5,554,753 A | 9/1996 | O'Donnell et al. |
| 5,840,739 A | 11/1998 | Bergeron, Jr. |
| 5,872,259 A | 2/1999 | Reuter |
| 5,929,232 A | 7/1999 | Jacobsen et al. |
| 6,083,966 A | 7/2000 | Bergeron, Jr. |
| 6,159,983 A | 12/2000 | Bergeron, Jr. |
| 6,383,233 B1 | 5/2002 | Reuter |
| 6,428,583 B1 | 8/2002 | Reuter |
| 6,521,652 B1 | 2/2003 | Bergeron |
| 6,525,080 B1 | 2/2003 | Bergeron |
| 6,559,315 B1 | 5/2003 | Bergeron |
| 6,982,335 B2 | 1/2006 | Chorghade et al. |
| 2003/0088105 A1 | 5/2003 | Krich et al. |
| 2003/0220504 A1 | 11/2003 | Chorghade et al. |
| 2003/0225287 A1 | 12/2003 | Chorghade et al. |
| 2003/0229231 A1 | 12/2003 | Chorghade et al. |
| 2003/0236404 A1 | 12/2003 | Gimi et al. |
| 2003/0236426 A1 | 12/2003 | Chorghade et al. |
| 2003/0236434 A1 | 12/2003 | Gimi et al. |
| 2003/0236435 A1 | 12/2003 | Gimi et al. |
| 2004/0002613 A1 | 1/2004 | Chorghade et al. |
| 2004/0006224 A1 | 1/2004 | Chorghade et al. |
| 2004/0024224 A1 | 2/2004 | Chorghade et al. |

FOREIGN PATENT DOCUMENTS

| | | |
|---|---|---|
| DE | 20 20 866 A | 11/1971 |
| DE | 30 02 989 A1 | 7/1981 |
| EP | 1 302 467 A2 | 4/2003 |
| GB | 1 292 170 | 10/1972 |
| WO | WO 94/11367 A1 | 5/1994 |
| WO | WO 97/36885 A1 | 10/1997 |
| WO | WO 00/01670 A1 | 1/2000 |
| WO | WO 00/12493 A1 | 3/2000 |
| WO | WO 00/16763 A2 | 3/2000 |

OTHER PUBLICATIONS

Ehrler, Juerg, and Farooq, Saleem, "Total Synthesis of Thiangazole," *Synlett*, 702-704 (1994).

(Continued)

*Primary Examiner*—Kamal A. Saeed
(74) *Attorney, Agent, or Firm*—Hamilton, Brook, Smith & Reynolds, P.C.

(57) ABSTRACT

A useful and efficient method of preparing an alkylated thiazoline carboxylic acid, or a derivative thereof, comprises coupling a substituted aryl nitrile such as, for example, 2,4-dimethoxybenzonitrile or 4-methoxybenzonitrile, with a cysteine ester to form a substituted thiazoline carboxylic acid ester; optionally hydrolyzing the substituted thiazoline carboxylic acid ester to form a substituted thiazoline carboxylic acid; optionally, protecting the carboxyl group; alkylating the thiazoline ring at the 4-carbon position, as indicated in Structural Formula (I), with a compound of the formula $R_1$-L, wherein $R_1$ is as defined above and L is a leaving group, in the presence of a phase transfer catalyst; and, optionally, deprotecting the carboxyl group.

In one embodiment of the present invention, a cinchona-alkaloid derived phase transfer catalyst is used to alkylate a protected substituted thiazoline carboxylic acid.

20 Claims, No Drawings

OTHER PUBLICATIONS

Kishore, V., et al., "Synthesis of α-Poly-[$N^E$-(2-aryl-$\Delta^2$-thiazoline-4-carbonyl)-$_L$-lysines] With Antiviral Acitivity," *Indian Journal of Chemistry 15B:* 255-257 (1977).

Zamri, Adel, and Abdallah, Mohamed A., "An Improved Stereocontrolled Synthesis of Pyochelin, Siderophore of *Pseudomonas aeruginosa* and *Burkholderia cepacia,*" *Tetrahedron* 56: 249-256 (2000).

Bergeron, R., et al., "Desazadesmethyldesferrithiocin Analogues as Orally Effective Iron Chelators," *J. Med. Chem.,* 42:95-108 (1999).

Bergeron, R. et al., "The Desferrithiocin Pharmacophore," *J. Med. Chem.,* 37:1411-1417 (1994).

Bergeron, R. et al., "Effects of C-4 Stereochemistry and C-4 Hydroxylation on the Iron Clearing Efficiency and Toxicity of Desferrithiocin Analogues," *J. Med. Chem.,* 42:2432-2440 (1999).

Bergeron, R. et al., "Synthesis and Biological Evaluation of Naphthyldesferrithiocin Iron Chelators," *J. Med. Chem.,* 39:1575-1581 (1996).

Bergeron, R. et al., "Evaluation of Desferrithiocin and Its Synthetic Analogues as Orally Effective Iron Chelators," *J. Med. Chem.,* 34:2072-2078 (1991).

Bergeron, R. et al., "Evaluation of the Desferrithiocin Pharmacophore as a Vector for Hydroxamates," *J. Med. Chem.,* 42:2881-2886 (1999).

Bergeron, R. et al., "An Investigation of Desferrithiocin Metabolism," *J. Med. Chem.,* 37:2889-2895 (1994).

Bergeron, R. et al., "A Comparative Study of the Iron-Clearing Properties of Desferrithiocin Analogues with Desferrioxamine B in a *Cebus* Monkey Model," *Blood,* 81(8):2166-2173 (1993).

Bergeron, R. et al., "Pharmacokinetics of Orally Administered Desferrithiocin Analogs in *Cebus Apella* Primates," *Drug Metabolism and Disposition,* 27(12):1496-1498 (1999).

Corey, E. J., et al., "A Rational Approach to Catalytic Enantioselective Enaolate Alkylation Using a Structurally Rigidified and Defined Chiral Quaternary Ammonium Salt Under Phase Transfer Conditions," *J. Am. Chem. Soc.,* 119:12414-12415 (1997).

Mulqueen, G. C., et al., "Synthesis of the Thiazoline-based Siderophore (S)-Desferrithiocin," *Tetrahedron,* 49(23):5359-5364 (1993).

O'Donnell, M. J., et al., "α-Methyl Amino Acids by Catalytic Phase-Transfer Aklylations," *Tetrahedron Letters,* 23(41):4259-4262 (1982).

SYNTHESIS OF SUBSTITUTED THIAZOLINE CARBOXYLIC ACIDS

RELATED APPLICATIONS

This application is a continuation of U.S. patent application Ser. No. 10/439,263 filed on May 15, 2003 (now U.S. Pat. No. 6,982,335), which claims the benefit of U.S. Provisional Application Nos. 60/381,012, 60/381,021, 60/380,894, 60/380,910, 60/380,880, 60/381,017, 60/380,895, 60/380,903, 60/381,013, 60/380,878 and 60/380,909, all of which were filed May 15, 2002. U.S. patent application Ser. No. 10/439,263 also claims the benefit of U.S. Provisional Application No. 60/392,833, filed Jun. 27, 2002. The entire teachings of the above-referenced applications are incorporated herein by reference.

BACKGROUND OF THE INVENTION

The use of desferrithiocin analogs for iron clearing has been described by Bergeron, et al in "Desazadesmethyldesferrithiocin Analogues as Orally Effective Iron Chelators," J. Med. Chem., vol. 42, no. 1, 95-108 (1999). Desferrithiocin and related compounds represent an advance in iron chelation therapy for subjects suffering from iron overload disorders. Present therapeutic agents, such as desferroxamine, require parenteral administration and have a very short half-life in the body, so that patient compliance and treatment cost are serious problems for subjects receiving long-term chelation therapy. Desferrithiocin and related compounds are effective when orally administered, thereby reducing patient compliance issues.

The iron clearing efficiency of desferrithiocin analogues has been shown to substantially depend on the stereochemistry at the C-4 position of the thiazoline ring. Desferrithiocin analogues based on (S)-enantiomers have been found to be especially active iron clearing agents in primates. See, for example, Bergeron, et al., "Effects of C-4 Stereochemistry and C-4' Hydroxylation on the Iron Clearing Efficiency and Toxicity of Desferrithiocin Analogues," J. Med. Chem., vol. 42, no. 13, 2432-2440 (1999).

(S)-Desferrithiocin analogues have been synthesized using the amino acid reagent D-cysteine, which is expensive compared to the naturally occurring L-cysteine isomer. U.S. Pat. Nos. 6,083,966 and 5,840,739, the entire teachings of which are incorporated by reference herein, describe thiazoline acid derivatives including those synthesized from D-cysteine.

Therefore, there is a need for novel methods of producing desferrithiocin analogues at a reasonable cost, and also for means of isolating desired enantiomers. In particular, there is a need for novel methods of producing the iron clearing compound 4,5-dihydro-2-(2,4-dihydroxyphenyl)-4-methylthiazole-4(S)-carboxylic acid at a reasonable cost.

SUMMARY OF THE INVENTION

In one aspect, the present invention relates to a method of preparing an alkylated thiazoline carboxylic acid or a derivative thereof represented by Structural Formula (I):

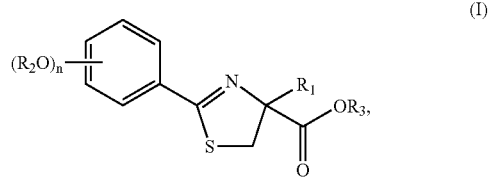

(I)

or a salt thereof, wherein $R_1$ is a substituted or unsubstituted alkyl group; each $R_2$ is, independently, —H or a substituted or unsubstituted alkyl group; $R_3$ is —H, a substituted or unsubstituted alkyl group, or a carboxyl protecting group; and n is an integer from 1 to 5, the method comprising:

(a) coupling a compound represented by Structural Formula (II):

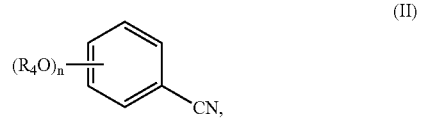

(II)

wherein each $R_4$ is, independently, a substituted or unsubstituted alkyl group and n is an integer from 1 to 5, with a cysteine ester represented by Structural Formula (III):

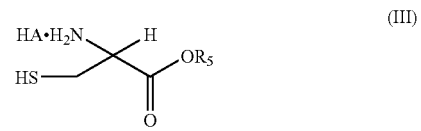

(III)

wherein A is an anion (e.g., carboxylates, sulfonates), preferably a halogen such as chloride, bromide or iodine, and $R_5$ is a substituted or unsubstituted alkyl group, thereby forming a substituted thiazoline carboxylic acid ester represented by Structural Formula (IV):

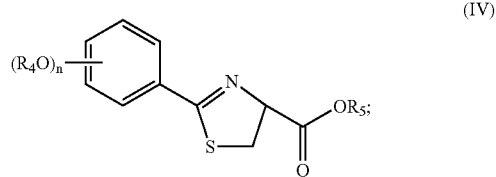

(IV)

(b) optionally, hydrolyzing the substituted thiazoline carboxylic acid ester to form a substituted thiazoline carboxylic acid represented by Structural Formula (V):

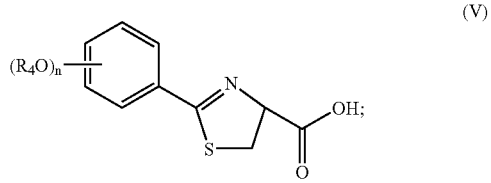

(V)

(c) optionally, protecting the carboxyl group of the substituted thiazoline carboxylic acid to form a protected thiazoline carboxylic acid represented by Structural Formula (VI):

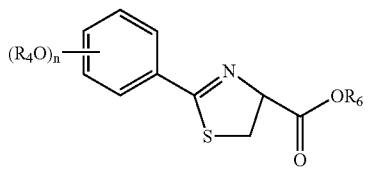

wherein $R_6$ is a carboxyl protecting group;

(d) alkylating the optionally protected thiazoline carboxylic acid represented by Structural Formula (VII):

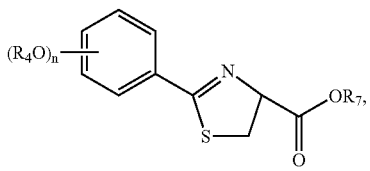

wherein $R_4$ and n are as defined above and $R_7$ is —H, $R_5$ or $R_6$ (preferably $R_6$ or an $R_5$ that is a carboxyl protecting group), with a compound having the formula $R_1$-L, wherein $R_1$ is defined as above and L is a leaving group, in the presence of a phase transfer catalyst to form an optionally alkylated protected thiazoline carboxylic acid represented by Structural Formula (VIII):

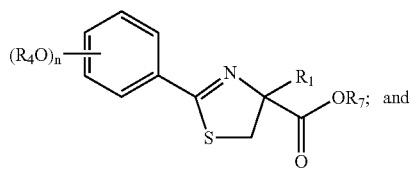

(e) optionally, hydrolyzing the optionally protected alkylated thiazoline carboxylic acid and cleaving ether groups represented by $R_4$ to form an alkylated thiazoline carboxylic acid.

The alkylated thiazoline carboxylic acid or the protected alkylated thiazoline carboxylic acid can be the (R) or (S)-isomer or a mixture thereof. The above methods can additionally comprise the step of purifying or ultrapurifying the product by further resolving the enantiomers or diastereomers of the alkylated thiazoline carboxylic acid or a derivative thereof. Additionally, the methods can comprise the isolation of the enantiomers of the synthesis products. Preferably, the (S)-enantiomer of the alkylated thiazoline carboxylic acid, or derivative thereof, is isolated.

In another aspect, the present invention relates to a method of preparing a compound represented by Structural Formula (XI):

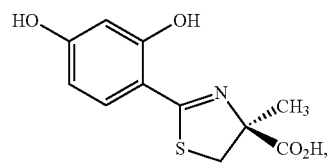

or a salt thereof, the method comprising:

(a) coupling a compound represented by Structural Formula (XII):

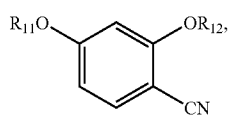

wherein $R_{11}$ and $R_{12}$ are independently, a C1 to C4 substituted or unsubstituted alkyl group, with a cysteine ester represented by Structural Formula (XIII):

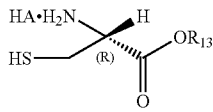

wherein A is an anion, preferably a halide such as chloride, bromide or iodine, and $R_{13}$ is a substituted or unsubstituted alkyl group; thereby forming a substituted thiazoline carboxylic acid ester represented by Structural Formula (XIV):

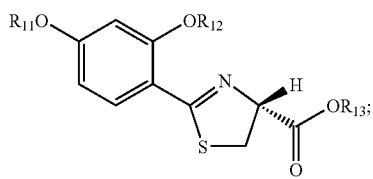

(b) optionally, hydrolyzing the substituted thiazoline carboxylic acid ester to form a substituted thiazoline carboxylic acid represented by Structural Formula (XV):

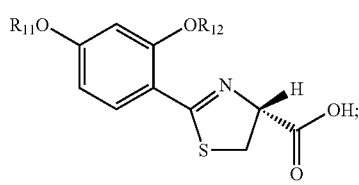

(c) optionally, protecting the carboxyl group of the substituted thiazoline carboxylic acid to form a protected thiazoline carboxylic acid represented by Structural Formula (XVI):

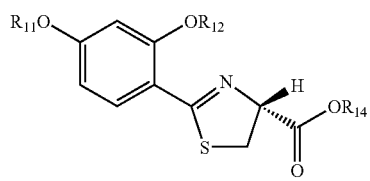

wherein $R_{14}$ is a carboxyl protecting group;

(d) alkylating the optionally protected thiazoline carboxylic acid represented by Structural Formula (XVII):

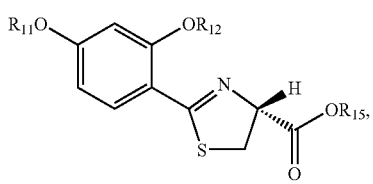

wherein $R_{15}$ is —H, $R_{13}$ or $R_{14}$ (preferably $R_{14}$ or an $R_{13}$ that is a carboxyl protecting group), with a compound having the formula $CH_3$-L, wherein L is a leaving group, in the presence of a phase transfer catalyst represented by Structural Formula (XVIII):

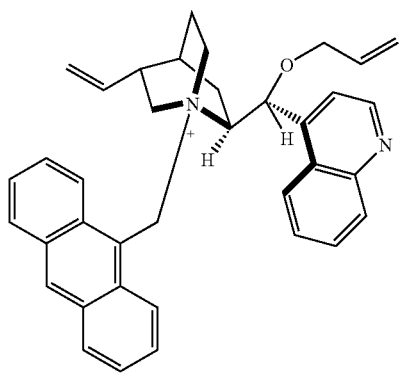

wherein X is a halogen, thereby forming an alkylated protected thiazoline carboxylic acid represented by Structural Formula (XIX):

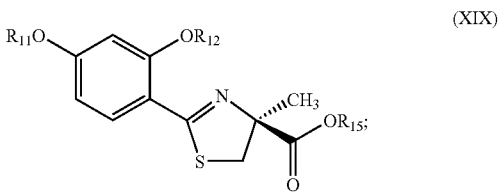

(e) hydrolyzing the protected alkylated thiazoline carboxylic acid and cleaving ether groups represented by $R_{11}$ and $R_{12}$ to form the compound represented by Structural Formula (XX):

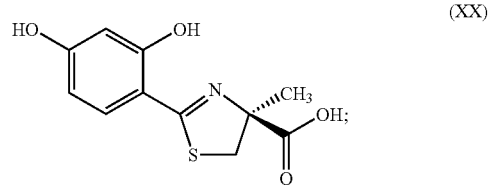

(f) optionally, purifying the (S)-isomer of the compound represented by Structural Formula (XX).

In yet another aspect, the present invention includes a method of preparing an alkylated thiazoline carboxylic acid represented by Structural Formula (XXI):

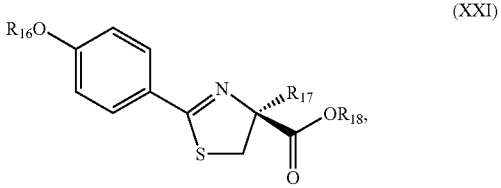

or a salt thereof, wherein $R_{16}$ is —H or a substituted or unsubstituted alkyl group; $R_{17}$ is a substituted or unsubstituted alkyl group, a substituted or unsubstituted aromatic group, or a substituted or unsubstituted heterocyclic group; and $R_{18}$ is —H, a substituted or unsubstituted alkyl group, or a carboxyl protecting group, the method comprising:

(a) coupling a compound represented by Structural Formula (XXII):

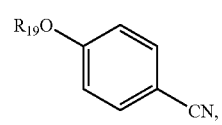

wherein $R_{19}$ is a C1 to C4 substituted or unsubstituted alkyl group,
with a cysteine ester represented by Structural Formula (XXIII):

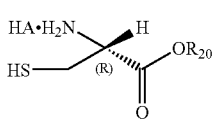

(XXIII)

wherein A is an anion, preferably a halide such as chloride, bromide or iodide, and $R_{20}$ is a substituted or unsubstituted alkyl group; thereby forming a substituted thiazoline carboxylic acid ester represented by Structural Formula (XXIV):

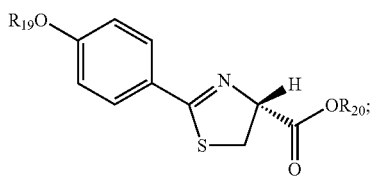

(XXIV)

(b) optionally, hydrolyzing the substituted thiazoline carboxylic acid ester to form a substituted thiazoline carboxylic acid represented by Structural Formula (XXV):

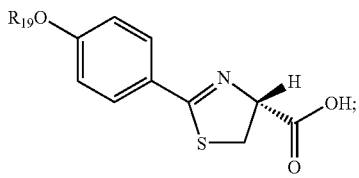

(XXV)

(c) optionally, protecting the carboxyl group of the substituted thiazoline carboxylic acid to form a protected thiazoline carboxylic acid represented by Structural Formula (XXVI):

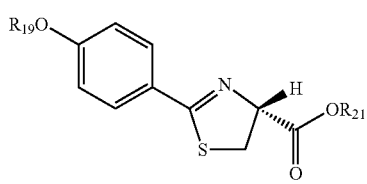

(XXVI)

wherein $R_{21}$ is a carboxyl protecting group;
(d) alkylating the optionally protected thiazoline carboxylic acid represented by Structural Formula (XXVII):

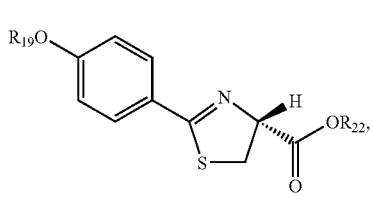

(XXVII)

wherein $R_{22}$ is —H, $R_{21}$ or $R_{22}$ (preferably $R_{22}$ or an $R_{21}$ that is a carboxyl protecting group),
with a compound having the formula $R_{17}$-L, wherein $R_{17}$ is defined as above and L is a leaving group, in the presence of a phase transfer catalyst thereby forming an alkylated optionally protected thiazoline carboxylic acid represented by Structural Formula (XXVIII):

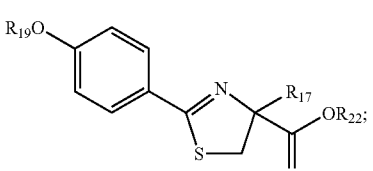

(XXVIII)

(e) optionally, hydrolyzing the optionally protected alkylated thiazoline carboxylic acid and cleaving ether groups to form the compound represented by Structural Formula (XXIX):

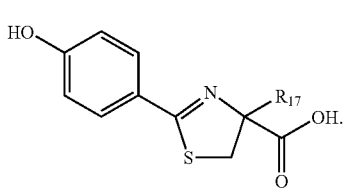

(XXIX)

Advantages of the present invention include the facile synthesis of a 2-(hydroxyphenyl)-4-alkyl-4,5-dihydro-thiazole-4-carboxylic acid or a 2-(alkoxyphenyl)-4-alkyl-4,5-dihydro-thiazole-4-carboxylic acid, represented by Structural Formula (I), from readily available substituted aryl nitrile compounds such as, for example, 2,4-dimethoxybenzonitrile or 4-methoxybenzonitrile. In particular, practice of the present invention allows the facile synthesis of 4'-hydroxydesazadesferrithiocin, also referred to as 4,5-dihydro-2-(2,4-dihydroxyphenyl)-4-methylthiazole-4(S)-carboxylic acid, an iron chelating agent.

DETAILED DESCRIPTION OF THE INVENTION

The present invention provides a useful and efficient method of preparing an alkylated thiazoline carboxylic acid, or a derivative thereof, represented by Structural Formula (I):

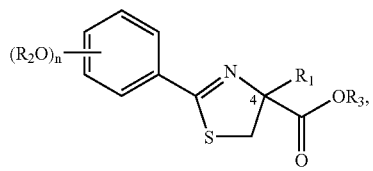

(I)

wherein $R_1$ is a substituted or unsubstituted alkyl group; each $R_2$ is, independently, —H or a substituted or unsubstituted alkyl group; $R_3$ is —H, a substituted or unsubstituted alkyl group or a carboxyl protecting group; and n is an integer from 1 to 5. Independently, each $R_2$ can be, for example, a substituted or unsubstituted C1 to C4 alkyl group. In a preferred embodiment, each $R_2$ is methyl. Also, each $R_2$ is preferably hydrogen. $R_3$ can be, for example, a substituted or unsubstituted C1 to C4 alkyl group. In a preferred embodiment, a group protecting an alkylated thiazoline carboxylic acid is removed and $R_3$ is then hydrogen.

The method of the instant invention comprises coupling a substituted aryl nitrile such as, for example, 2,4-dimethoxybenzonitrile or 4-methoxybenzonitrile, with a cysteine ester to form a substituted thiazoline carboxylic acid ester; optionally hydrolyzing the substituted thiazoline carboxylic acid ester to form a substituted thiazoline carboxylic acid; optionally, protecting the carboxyl group; alkylating the thiazoline ring at the 4-carbon position, as indicated in Structural Formula (I), with a compound of the formula $R_1$-L, wherein $R_1$ is as defined above and L is a leaving group, in the presence of a phase transfer catalyst; and, optionally, deprotecting the carboxyl group.

For example, the instant invention provides a method for producing a 2-(2,4-dihydroxyphenyl)-4-alkyl-4,5-dihydro-thiazole-4-carboxylic acid, as represented by Structural Formula (XXX):

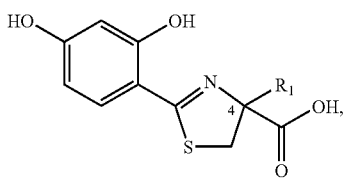

(XXX)

wherein $R_1$ is a substituted or unsubstituted alkyl group (e.g., methyl), that comprises coupling a substituted aryl nitrile, such as 2,4-dimethoxybenzonitrile, with a cysteine ester to form a substituted thiazoline carboxylic acid ester; optionally hydrolyzing the substituted thiazoline carboxylic acid ester to form a substituted thiazoline carboxylic acid; optionally protecting the carboxyl group; alkylating the thiazoline ring at the 4-carbon position with a compound of the formula $R_1$-L, wherein $R_1$ is as defined above and L is a leaving group, in the presence of a phase transfer catalyst; and deprotecting the carboxyl group. Also, the ether linkages (methoxy groups) or the phenyl ring are preferably cleaved to give free hydroxyl groups.

In one incarnation of the present invention, a cinchona-alkaloid derived phase transfer catalyst is used to alkylate a protected thiazoline carboxylic acid. Enantiomeric excesses of either (R) or (S)-stereoisomers are produced during the synthesis of the alkylated thiazoline carboxylic acid, or derivative thereof, due to the asymmetric alkylation of the protected thiazoline carboxylic acid. For example, one synthesis route will produce an enantiomeric excess of a protected 2-(2,4-dialkyoxyphenyl)-4-alkyl-4,5-dihydro-thiazole-4-(S)-carboxylic acid. Subsequently, the synthesis product can be purified by further resolving the enantiomers of the alkylated thiazoline carboxylic acid and isolating the desired isomer.

In one aspect of the present invention, an aryl nitrile and a cysteine ester are condensed to form a substituted thiazoline carboxylic acid ester. Preferred aryl nitrites include aryl nitrites where the aryl group is a substituted or unsubstituted phenyl group.

An aryl nitrile such as that represented by Structural Formula (II):

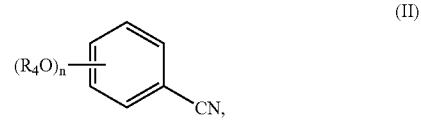

(II)

wherein each $R_4$ is, independently, a substituted or unsubstituted alkyl group and n is 1 to 5, can be coupled with a cysteine ester to form a substituted thiazoline carboxylic acid ester. Each $R_4$ can be, independently, a substituted or unsubstituted C1 to C4 alkyl group. Preferably, each $R_4$ is methyl. In one embodiment, the aryl nitrile is a 2,4-dialkoxybenzonitrile, preferably 2,4-dimethoxybenzonitrile. In another embodiment, the aryl nitrile is a 4-alkoxybenzonitrile, preferably 4-methoxybenzonitrile.

The aryl nitrile can be coupled with a cysteine ester, as represented by Structural Formula (III):

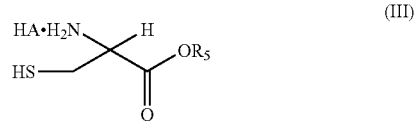

(III)

wherein A is an anion, preferably a halide such as chloride, bromide or iodide, and $R_5$ is a substituted or unsubstituted alkyl group, to form an ester of a substituted thiazoline carboxylic acid.

For example, a 2,4-dialkoxybenzonitrile, represented by Structual Formula (XXXI):

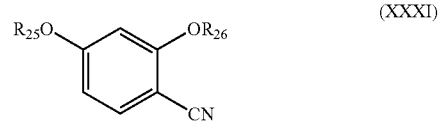

(XXXI)

wherein $R_{25}$ and $R_{26}$ are independently, a substituted or unsubstituted alkyl group, can be coupled with a cysteine ester to form a substituted thiazoline carboxylic acid ester. $R_{25}$ and $R_{26}$ can be, independently, a substituted or unsubstituted C1 to C4 alkyl group. Preferably, $R_{25}$ and $R_{26}$ are each methyl. In one embodiment, a 2,4-dialkoxybenzonitrile is coupled with a cysteine ester, as represented by Structural Formula (XXXII):

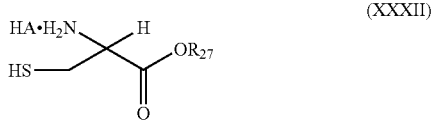

(XXXII)

wherein A is an anion, preferably a halide such as chloride, bromide or iodide, and $R_{27}$ is a substituted or unsubstituted alkyl group, to form an ester of a 2-(2,4-dialkoxyphenyl)-4,5-dihydro-thiazole-4-carboxylic acid. $R_{27}$ can be a C1 to C4 alkyl group. Preferably, $R_{27}$ is ethyl. In a preferred embodiment, the cysteine ester is the (R)-stereoisomer, for example, 2,4-dimethoxybenzonitrile is reacted with an (R)-cysteine ethyl ester to form ethyl 2-(2,4-dimethoxyphenyl)-4,5-dihydro-thiazole-4-(R)-carboxylate.

The condensation of an aryl nitrile and a cysteine ester typically occurs in a polar, protic solvent in the presence of an excess of base. Typically, the aryl nitrile and cysteine ester are refluxed together for several hours, such as 1-20 hours, 2-15 hours, 4-10 hours, or 6-8 hours. Refluxing preferably occurs in an inert atmosphere, such as nitrogen or argon. Suitable polar, protic solvents include, but are not limited to, water, methanol, ethanol, formic acid, acetic acid, dimethylformamide, N-ethylacetamide, formaldehyde diethyl acetal, and long chain alcohols (e.g., propanol and isopropanol). An alcohol, such as methanol or ethanol, is a preferred solvent. Suitable bases include secondary and tertiary amines such as dimethylamine, diethylamine, trimethylamine, triethylamine, diisopropylamine, and diisopropylethylamine. The base can be added in excess, such as one or more equivalents relative to the amount of cysteine ester. Suitable amounts of base have at least about one equivalent of base, and range from about 1 to about 10, about 1 to about 5, about 1 to about 3, or about 1 to about 2 equivalents, relative to the amount of cysteine ester. In one example, cysteine ethyl ester, 2,4-dimethoxybenzonitrile, and 5 equivalents of triethylamine are refluxed in ethanol to obtain ethyl 2-(2,4-dimethoxyphenyl)-4,5-dihydro-thiazole-4-carboxylate. In another example, cysteine ethyl ester, 4-methoxybenzonitrile, and 5 equivalents of triethylamine are refluxed in ethanol to obtain ethyl 2-(4-methoxyphenyl)-4,5-dihydro-thiazole-4-carboxylate.

Alternatively, an aryl imidate (e.g., a benzimidate, where the benzene ring can have one or more substituents, as described below) can be condensed with a cysteine ester to form a substituted thiazoline carboxylic acid ester. The substituted thiazoline carboxylic acid ester can be formed by coupling a substituted benzimidate such as, for example, 2,4-dihydroxybenzimidate, 2,4-dimethoxybenzimidate, or a 4-methoxybenzimidate, with a cysteine ester such as the cysteine ester represented by Structural Formula (XXXII). Typically, coupling of a cysteine ester or a 2-alkylcysteine ester with an aryl imidate includes reacting a cysteine ester (or a related compound) with the aryl imidate under basic conditions. Acceptable bases include trimethylamine, triethylamine, dimethylamine, diethylamine, diphenylamine, diisopropylamine; diisopropylethylamine; 1,4-diazabicyclo[2.2.2]octane (DABCO); 1,5-diazabicyclo-[4.3.0]-non-5-ene (DBN); and the like.

Aryl imidates can be prepared, for example, from aryl nitriles, aryl carboxylic acids, and aryl amides. Methods of forming aryl imidates are discussed in co-pending U.S. patent application Ser. No. 60/380,909, filed on May 15, 2002, the entire contents of which are incorporated herein by reference. In one example, an aryl carboxylic acid (e.g., benzoic acid) is converted into an acid chloride, then an amide, followed by reaction with a trialkyloxonium hexafluorophosphate or a trialkyloxonium tetrafluoroborate to form the aryl imidate. In a second example, an aryl nitrile is converted into an aryl imidate through reaction with an alcohol in the presence of an acid, as is described below.

The substituted thiazoline carboxylic acid esters represented by Structural Formulas (IV), (XIV), and (XXIV) can comprise a protected carboxyl group. Alternatively, the substituted thiazoline carboxylic acid ester can be protected by hydrolyzing the substituted thiazoline carboxylic acid ester represented by Structural Formulas (IV), (XIV) and (XXIV) and protecting the resulting substituted thiazoline carboxylic acid. In one aspect, the method of the present invention optionally comprises hydrolyzing a substituted thiazoline carboxylic acid ester to form a substituted thiazoline carboxylic acid as represented by Structural Formula (V). For example, the ester of a 2-(2,4-dialkoxyphenyl)-4,5-dihydro-thiazole-4-carboxylic acid can be hydrolyzed to form a substituted thiazoline carboxylic acid, such as a 2-(2,4-dialkoxyphenyl)-4,5-dihydro-thiazole-4-carboxylic acid such as the compound represented by Structural Formula (XV). Hydrolysis of carboxylic esters is well known in the art. Hydrolysis of carboxylic esters is typically accomplished through acid or base catalysis. The substituted thiazoline carboxylic acid ester can be reacted with water in the presence of a base to form the substituted thiazoline carboxylic acid. Preferably, the substituted thiazoline carboxylic acid ester is refluxed with aqueous sodium hydroxide in methyl tertiary-butyl ether (MTBE) to form a substituted thiazoline carboxylic acid.

A protecting group may be added to the carboxyl group of the substituted thiazoline carboxylic acid to form a protected thiazoline carboxylic acid. Carboxyl groups can be protected by means well known in the art. Carboxyl groups are typically protected as esters (e.g., —COOR' wherein R' can be substituted or unsubstituted C1 to C10 alkyl, up to C30 substituted or unsubstituted aryl or alkyl-aryl wherein the alkyl is substituted or unsubstituted C1 to C5 and the aryl is substituted or unsubstituted and up to C30), or as carboxamide groups (e.g., —CONR"R'" wherein R' and R'" can be, independently, —H, substituted or unsubstituted C1 to C10 alkyl, up to C30 substituted or unsubstituted aryl, or alkyl-aryl wherein the alkyl is substituted or unsubstituted C1 to C5 and the aryl is substituted or unsubstituted and up to C30). In one embodiment, the carboxyl group of the substituted thiazoline carboxylic acid is protected as an ester of the form —COOR$_7$ wherein R$_7$ is a carboxyl protecting group. Preferably, R$_7$ is an alkyl group. Even more preferred, R$_7$ is isopropyl. The protected thiazoline carboxylic acid ester may be formed through various means. An ester of a carboxylic acid can be produced using, for example, an alcohol, such as through the acid catalyzed reaction of a substituted thiazoline carboxylic acid with an alcohol. In a preferred embodiment, the protected thiazoline carboxylic acid is produced through the acid catalyzed reaction of a substituted thiazoline carboxylic acid with isopropanol. Common acid catalysts include sulfuric acid and p-toluenesulfonic acid. Alternatively, a substituted thiazoline carboxylic acid is treated with an alcohol in the presence of a coupling agent. Coupling agents include, but are not limited to dicyclohexylcarbodiimide (DCC); alkyl chloroformate and triethylamine; pyridinium salts and tributylamine; Amberlyst-15; phenyl dichlorophosphate; diethyl azoicarboxylate and triphenyl phosphine; DCC and an aminopyridine; 2-chloro-1,3,5-trinitrobenzene and pyridine; 1,1'-carbonylbis(3-methylimidazolium) triflate; di-2-pyridyl carbonate, polystyryl diphenylphosphine; (trimethylsilyl) ethoxyacetylene; chlorosulfonyl isocyanate; chlorosilanes, $MeSO_2Cl$-$Et_3N$; $Ph_3P$—$CCl_4$-$Et_3N$; and N,N'-carbonyldiimidazole. Preferably, dicyclohexylcarbodiimide (DCC) is the coupling agent. As an example, a substituted thiazoline carboxylic acid are treated with an alcohol, such as isopropanol; DCC; and 4-(dimethylamino)pyridine (DMAP) in tetrahydrofuran (THF) at room temperature to form a protected thiazoline carboxylic acid.

Additional protecting groups, methods of adding a protecting group, and methods of removing a protecting group are taught in "Protective Groups in Organic Synthesis, 3$^{rd}$ Edition" by Peter G. M. Wuts and Theodora W. Greene, Wiley-Interscience, 1999, the entire contents of which are incorporated herein by reference.

In one embodiment, the protected thiazoline carboxylic acid represented by Structural Formula (VII) can be alkylated in the presence of one or more bases, an alkylating agent, and a phase transfer catalyst. For example, isopropyl-2-(2,4-dimethoxyphenyl)-4,5-dihydro-thiazole-4-carboxylate or isopropyl-2-(4-methoxyphenyl)-4,5-dihydro-thiazole-4-carboxylate is reacted with 50% potassium hydroxide and excess methyl iodide in dichloromethane in the presence of a phase transfer catalyst at a temperature of about −80° C. to about room temperature. Preferably, the protected thiazoline carboxylic acid is alkylated using a phase transfer catalyst such that an enantiomeric excess of either the (R) or (S)-isomer is produced, i.e., the alkylation is stereoselective.

Alkylating agents can have the formula $R_1$-L, where $R_1$ is a substituted or unsubstituted alkyl group and L is a leaving group. Preferred $R_1$ groups include substituted or unsubstituted C1-C4 alkyl groups, for example, methyl or benzyl. The leaving group L is typically a weak base. Suitable leaving groups include halogen, tosyl, mesyl, triflyl, brosyl, p-nitrophenyl, and 2,4-dinitrophenyl groups. Halogens include bromine, chlorine, and iodine. Iodine is a preferred leaving group. Suitable amounts of alkylating agent can include about 1 to 20, about 2 to 15, about 3 to 10, or, preferably, about 5 equivalents, relative to the amount of protected thiazoline carboxylic acid.

Preferred bases include alkali or alkaline earth metal hydroxides, alkoxides, amides, or carbonates or their combinations. Available bases include potassium t-butoxide, sodium methoxide, sodium ethoxide, sodium amide, calcium carbonate, cesium carbonate, and the alkali metal salts of hexamethyl disilazide (HMDS). Preferred bases include potassium hydroxide, sodium hydroxide, and cesium hydroxide monohydate. Suitable amounts of base include about 5 to 25, about 10 to 20, about 10 to 15, or, preferably, about 10 equivalents, relative to the amount of protected thiazoline carboxylic acid.

The organic phase of the process can include any organic solvent which is substantially inert to the catalyst, reactants and products. The organic phase may comprise a combination of two or more solvents. Solvents generally include, but are not limited to, aprotic solvents such as acetonitrile, acetone, dimethylformamide, dimethyl sulfoxide, tetrahydrofuran, and hexamethylphosphoramide. In one embodiment, the organic phase comprises toluene. In a preferred embodiment, the organic phase comprises dichloromethane.

The alkylation of the protected thiazoline carboxylic acid can be performed at temperatures ranging from about −80° C. to about room temperature such as between about −80° and 0° C. In a preferred embodiment, the alkylation is performed at temperatures of between about −80° and −40° C., for example, at about −60° C.

In one aspect of the present invention, a cinchona-alkaloid derived phase transfer catalyst is used to alkylate a protected substituted thiazoline carboxylic acid. In one particular embodiment, a cinchona-alkaloid derived phase transfer catalyst is used to alkylate a protected 2-(alkoxyphenyl)-4,5-dihydro-thiazole-4-carboxylic acid, represented by Structural Formula (VII) (e.g., a protected 2-(2,4-dialkoxyphenyl)-4,5-dihydro-thiazole-4-carboxylic acid or a protected 2-(4-alkoxyphenyl)-4,5-dihydro-thiazole-4-carboxylic acid), at the thiazoline 4-position. The phase transfer catalyst can be derived from cinchonine or from cinchonidine. Use of one of these catalysts in the alkylation reaction can yield enantiomeric excesses of either the (R) or (S)-enantiomer of the alkylated protected thiazoline carboxylic acid, while use of an enantiomer of that catalyst can yield enantiomeric excesses of the other enantiomer of the alkylated cysteine derivative. Thus by selecting the phase transfer catalyst used, one can direct which enantiomer of the alkylated cysteine derivative will form.

In a preferred embodiment, the phase transfer catalyst used is derived from cinchonidine and is represented by Structural Formula (IX):

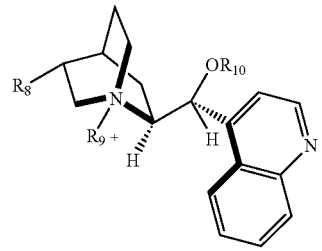

(IX)

wherein $R_8$ and $R_{10}$ are, independently, —H, a substituted or unsubstituted alkyl group, a substituted or unsubstituted aromatic group, or a substituted or unsubstituted heterocyclic group, or a salt thereof;

$R_9$ is a substituted or unsubstituted alkyl group, a substituted or unsubstituted aromatic group, or a substituted or unsubstituted heterocyclic group, or a salt thereof; and X is a halogen.

In one preferred embodiment, $R_8$ is substituted or unsubstituted ethenyl. $R_9$ can be, for example, substituted or unsubstituted napthyl, anthracenylmethyl, or benzyl. Preferably, $R_9$ is 9-anthracenylmethyl, represented by Structural Formula (X):

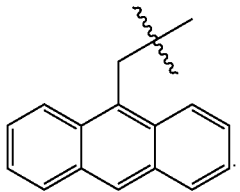

(X)

$R_{10}$ can be, for example, substituted or unsubstituted allyl or benzyl. $R_{10}$ is preferably substituted or unsubstituted allyl. X is preferably chlorine or bromine. Thus, the phase transfer catalyst can be represented by Structural Formula (XVIII):

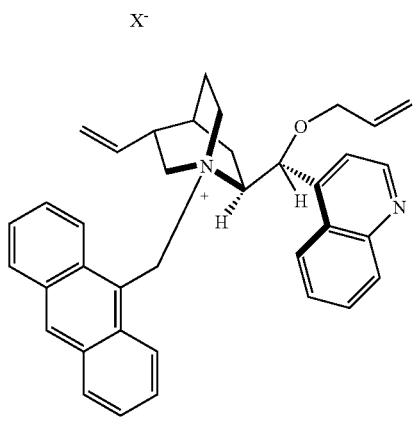

(XVIII)

Additional examples of phase transfer catalysts suitable for use in the present invention are described in U.S. Pat. No. 5,554,753 issued to O'Donnell, et al., the entire teachings of which are incorporated herein by reference.

The phase transfer catalyst represented by Structural Formula (XVIII) is preferably prepared using the following method as described by Corey, et al., in "A Rational Approach to Catalytic Enantioselective Enolate Alkylation Using a Structurally Rigidified and Defined Chiral Quaternary Ammonium Salt Under Phase Transfer Conditions" (J. Am. Chem. Soc. 119, 12414-12415 and Corey Supplemental therein 1-25 (1997)), the entire contents of which are incorporated by reference herein by reference. In that method, cinchonidine, represented by Structural Formula (XXXIII):

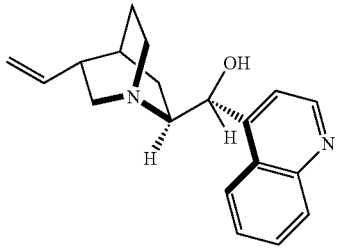

(XXXIII)

is suspended in toluene and 9-(chloromethyl)anthracene, represented by Structural Formula (XXXIV):

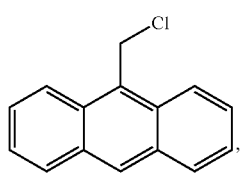

(XXXIV)

is added. The mixture is stirred at reflux for about 2 hours. The product, N-9-anthracenylmethylcinchonidinium chloride represented by Structural Formula (XXXV):

(XXXV)

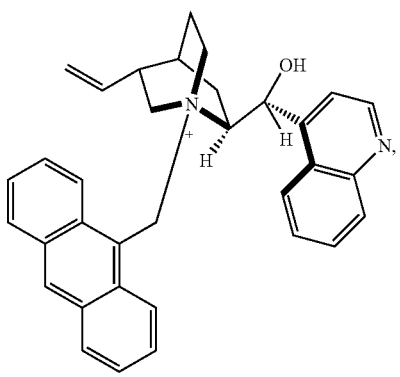

is collected as a light yellow solid. The N-9-anthracenylmethylcinchonidinium chloride is then suspended in dichloromethane. To this suspension is added 50% KOH and allyl bromide. The resulting mixture is then stirred for about 4 hours at about 23° C. The product, O(9)-allyl-N-9-anthracenylmethylcinchonidium bromide represented by Structural Formula (XVIII), wherein X is bromine, is collected as a light orange solid.

The use of O(9)-allyl-N-9-anthracenylmethylcinchonidium bromide as a phase transfer catalyst is also described in U.S. patent application Ser. No. 60/381,012, filed on May 15, 2002, the entire contents of which are incorporated herein by reference.

The phase transfer catalyst represented by Structural Formula (XXXVI):

(XXXVI)

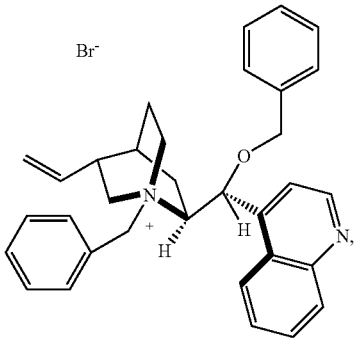

is also suitable for the purposes of the instant invention.

Examples of other phase transfer catalysts include benzyl triethyl ammonium chloride, benzyl trimethyl ammonium chloride, benzyl tributyl ammonium chloride, tetrabutyl ammonium bromide, tetraethyl ammonium bromide, tetrabutyl ammonium hydrogen sulfate, tetramethyl ammonium iodide, tetramethyl ammonium chloride, triethylbutyl ammonium bromide, tributyl ethyl ammonium bromide, tributyl methyl ammonium chloride, 2-chloroethylamine chloride HCl, bis(2-chloroethyl)amine HCl, 2-dimethylaminoethyl chloride HCl, 2-ethylaminoethyl chloride HCl, 3-dimethylaminopropyl chloride HCl, monoethylamine HCl, diethylamine HCl, triethylamine HCl, ethanolamine HCl, diethanolamine HCl, triethanolamine HCl, cyclohexylamine HCl, dicyclohexylamine HCl, cyclohexylamine HCl, diisopropylethylamine HCl, ethylenediamine HCl, and aniline HCl.

In one form of the present invention, the phase transfer catalyst, such as O(9)-allyl-N-9-anthracenylmethylcinchonidium bromide, is present in an amount of about 0.05 to 0.4 equivalents relative to the amount of protected thiazoline carboxylic acid. Alternatively, the phase transfer catalyst can be present between about 0.05 and 0.25, between about 0.1 and 0.15, or, preferably, at about 0.1 equivalents (relative to the amount of protected thiazoline carboxylic acid).

In a preferred embodiment, isopropyl 4,5-dihydro-2-(2,4-dimethoxyphenyl)-thiazole-4-carboxylate is reacted with 50% potassium hydroxide and excess methyl iodide in dichloromethane in the presence of about 10% (mol) of O(9)-allyl-N-9-anthracenylmethylcinchonidium bromide.

Subsequent to the alkylation, the group protecting the carboxyl group of the alkylated protected thiazoline carboxylic acid can be removed. Additionally, ether groups present on the alkylated protected thiazoline carboxylic acid can be cleaved. Methods of cleaving ether groups are well known in the art. For example, ether groups can be cleaved by reacting the ether compound with an excess of hydrogen bromide or hydrogen iodide. Ether groups also can be cleaved by reacting the ether compound with boron tribromide ($BBr_3$), methylmagnesium iodide ($CH_3MgI$), or aluminum trichloride ($AlCl_3$). In a preferred embodiment of the present invention, an alkylated protected thiazoline carboxylic acid is hydrolyzed, as described above, and its ether groups cleaved to form an alkylated thiazoline carboxylic acid, such as 2-(2,4-dihydroxyphenyl)-4-alkyl-4,5-dihydro-thiazole-4-carboxylic acid.

The products, either enantiomers or diastereomers, of the above described syntheses can be further purified or ultra-purified before or after any protecting groups are removed. In one embodiment, a protected or unprotected 2-(2,4-dialkoxyphenyl)-4-alkyl-4,5-dihydro-thiazole-4-carboxylic acid or 2-(2,4-dihydroxyphenyl)-4-alkyl-4,5-dihydrothiazole-4-carboxylic acid is purified by further resolution into (R) and (S)-isomers based on the thiazoline 4-carbon. For example, the unprotected 2-(2,4-dialkoxyphenyl)-4-alkyl-4,5-dihydro-thiazole-4-carboxylic acid or or 2-(2,4-dihydroxyphenyl)-4-alkyl-4,5-dihydrothiazole-4-carboxylic acid can be further resolved using the technique of emulsion crystallization or by the formation of a diastereomeric salt. Preferably, following resolution, the (S)-isomer of the alkylated thiazoline carboxylic acid, for example, a 2-(2,4-dialkoxyphenyl)-4-alkyl-4,5-dihydro-thiazole-4(S)-carboxylic acid, is isolated.

Chiral carboxylic acids, such as a 2-(alkoxyphenyl)-4-alkyl-4,5-dihydro-thiazole-4-carboxylic acid, can further resolved by forming a diastereomeric salt with the chiral carboxylic acid and a chiral amine. Suitable chiral amines include arylalkylamines such as 1-alkyl-1-aminoalkanes and 1-aryl-1-aminoalkanes. Examples include (R)-1-phenylethylamine, (S)-1-phenylethylamine, (R)-1-tolylethylamine, (S)-1-tolylethylamine, (R)-1-phenylpropylamine, (S)-1-propylamine, (R)-1-tolylpropylamine, and (S)-1-tolylpropylamine. Preferably, (R)-1-phenylethylamine (i.e., (R)-1-phenyl-1-aminoethane) is used to further resolve the chiral carboxylic acid mixture. Resolution of chiral compounds using diastereomeric salts is further described in *CRC Handbook of Optical Resolutions via Diastereomeric Salt Formation* by David Kozma (CRC Press, 2001), incorporated herein by reference in its entirety.

Chiral carboxylic acids, such as a 2-(alkoxyphenyl)-4-alkyl-4,5-dihydro-thiazole-4-carboxylic acid, can be also be purified through further resolution by emulsion crystallization, as described in U.S. Pat. Nos. 5,872,259, 6,383,233 and 6,428,583 issued to Reuter, the teachings of which are incorporated herein in their entirety by reference. Briefly, emulsion crystallization is a process for separating a desired substance from an aggregate mixture. The process involves forming a three phase system, the first phase comprising the aggregate mixture, the second phase being liquid and comprising a transport phase, and the third phase comprising a surface upon which the desired substance can crystallize. A chemical potential exists for crystal growth of the desired substance in the third phase of the system, thereby creating a flow of the desired substance from the first phase through the second phase to the third phase, where the desired substance crystallizes and whereby an equilibrium of the activities of the remaining substances in the aggregate mixture is maintained between the first phase and the second phase.

In one example of emulsion crystallization, a solution of a racemic mixture is supersaturated (by either cooling, adding a solvent in which one or more components are sparingly soluble or by evaporation of the solution). Ultrasonication typically aids the process of forming an emulsion. The mixture is then seeded with crystals of the desired, optically active acid along with an additional quantity of surfactant and an anti-foaming agent. The desired product usually crystallizes out and can be separated by filtration.

An alkyl group is a hydrocarbon in a molecule that is bonded to one other group in the molecule through a single covalent bond from one of its carbon atoms. Alkyl groups can be cyclic, branched or unbranched, and/or saturated or unsaturated. Typically, an alkyl group has one to about 24 carbons atoms, or one to about 12 carbon atoms. Lower alkyl groups have one to four carbon atoms and include methyl, ethyl, n-propyl, iso-propyl, n-butyl, sec-butyl and tert-butyl.

Aromatic (or aryl) groups include carbocyclic aromatic groups such as phenyl, p-tolyl, 1-naphthyl, 2-naphthyl, 1-anthracyl and 2-anthracyl. Aromatic groups also include heteroaromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl.

Aromatic groups also include fused polycyclic aromatic ring systems in which a carbocyclic, alicyclic, aromatic ring or heteroaryl ring is fused to one or more other heteroaryl or aryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl and 3-isoindolyl.

Suitable substituents for alkyl and aryl groups include —OH, halogen (—Br, —Cl, —I and —F), —O(R'), —O—CO—(R'), —CN, —NO$_2$, —COOH, =O, —NH$_2$, —NH(R'), —N(R')$_2$, —COO(R'), —CONH$_2$, —CONH(R'), —CON(R')$_2$, —SH, —S(R'), guanidine, alkyl, and aryl. Each R' is, independently, an alkyl group or an aromatic group. A substituted alkyl or aryl group can have more than one substituent.

Also included in the present invention are salts of the disclosed carboxylic acids. For example, carboxylic acids can also be present in the anionic, or conjugate base, form, in combination with a cation. Suitable cations include alkali metal ions, such as sodium and potassium ions; alkaline earth ions, such as calcium and magnesium ions; and unsubstituted and substituted (primary, secondary, tertiary and quaternary) ammonium ions. Suitable cations also include transition metal ions such as manganese, copper, nickel, iron, cobalt, and zinc. Basic groups such as amines can also be protonated with a counter anion, such as hydroxide, halogens (chloride, bromide, and iodide), acetate, formate, citrate, ascorbate, sulfate or phosphate.

Exemplification

EXAMPLE 1

Preparation of the Phase Transfer Catalyst

A cinchonidine derived phase transfer catalyst is prepared as follows. About 4 grams of cinchonidine is suspended in about 40 mL of toluene. About 3 grams of 9-(choloromethyl) anthracene is then added to the suspension. The mixture is heated to reflux and stirred for about 2 hours. Solids are cooled to room temperature, poured onto about 200 mL of diethyl ether and filtered. The product collected is N-9-anthracenylmethylcinchonidinium chloride.

About 5 grams N-9-anthracenylmethylcinchonidinium chloride is then suspended in about 40 mL dichloromethane. Then about 2.5 mL allyl bromide and about 5 mL of 50% KOH (aq) are added to the suspension. The mixture is stirred at about room temperature for about 4 hours. Fifty milliliters of water are then added to the mixture and the mixture is extracted using three aliquots of dichloromethane. The organic extracts are combined and dried over Na$_2$SO$_4$, filtered, and concentrated in vacuo. Recrystalization of the residue from methanol-diethyl ether at −20° C. yields the product, O(9)-allyl-N-9-anthracenylmethylcinchonidium bromide.

EXAMPLE 2

Preparation of 4,5-dihydro-2-(2,4-dihydroxyphenyl)-4-methyl-thiazole-4(S)-carboxylic Acid 2,4-Dimethoxybenzonitrile, (R)-cysteine ethyl ester and about 5 equivalents of triethylamine are refluxed in ethanol for about 6-8 hours to obtain ethyl-2-(2,4-dimethoxyphenyl)-4,5-dihydro-thiazole-4-(R)-carboxylate.

Ethyl-2-(2,4-dimethoxyphenyl)-4,5-dihydro-thiazole-4-(R)-carboxylate is refluxed with aqueous sodium hydroxide in methyl tertiary-butyl ether (MTBE) to form 2-(2,4-dimethoxyphenyl)-4,5-dihydro-thiazole-4-(R)-carboxylic acid.

Next, 2-(2,4-dimethoxyphenyl)-4,5-dihydro-thiazole-4-(R)-carboxylic acid is reacted with isopropanol; DCC; and 4-(dimethylamino)pyridine (DMAP) in tetrahydrofuran (THF) at room temperature to form isopropyl-2-(2,4-dimethoxyphenyl)-4,5-dihydro-thiazole-4-(R)-carboxylate.

Isopropyl-2-(2,4-dimethoxyphenyl)-4,5-dihydro-thiazole-4-carboxylate is reacted with 50% potassium hydroxide and excess methyl iodide in dichloromethane in the presence of O(9)-allyl-N-9-anthracenylmethylcinchonidium bromide to form isopropyl-2-(2,4-dimethoxyphenyl)-4-methyl-4,5-dihydro-thiazole-4-(S)-carboxylate in enantiomeric excess.

The isopropyl-2-(2,4-dimethoxyphenyl)-4-methyl-4,5-dihydro-thiazole-4-(S)-carboxylate is purified by further resolving the enantiomers using emulsion crystallization. Isopropyl-2-(2,4-dimethoxyphenyl)-4-methyl-4,5-dihydro-thiazole-4-(S)-carboxylate is then reacted with excess hydrochloric acid to form 2-(2,4-dihydroxyphenyl)-4-methyl-4,5-dihydro-thiazole-4-(S)-carboxylic acid.

EXAMPLE 3

Preparation of isopropyl 2-(4-methoxy-phenyl)-4,5-dihydro-thiazole-4-benzyl-4-carboxylate The C-4 benzylation of 2-(4-methoxy-phenyl)-4,5-dihydro-thiazole-4-carboxylic acid isopropyl ester (A) was performed as described below.

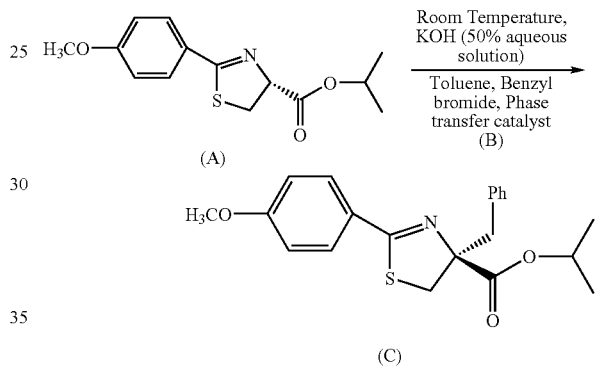

wherein the phase transfer catalyst (B) is represented by the following structural formula:

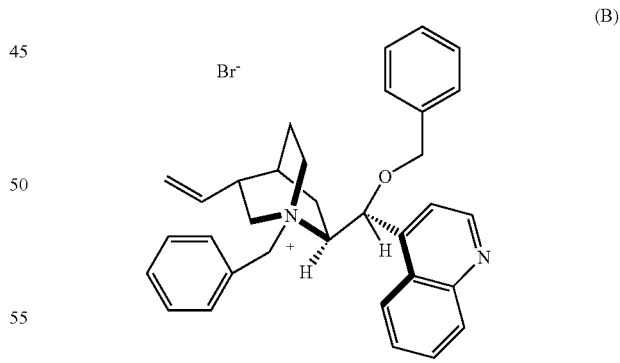

0.25 g of 2-(4-methoxy-phenyl)-4,5-dihydro-thiazole-4-carboxylic acid isopropyl ester (A) and 23 mg of phase transfer catalyst (B) were added to 25 milliliters of toluene. To this mixture, 1 milliliter of aqueous KOH (50%) was added and the mixture was stirred for approximately 15 minutes. 106 microliters of benzyl bromide (Avocado Research Chemicals Limited, Heysham, United Kingdom) was then added dropwise with stirring. The reaction was monitored using thin-layer chromatography (TLC) and left to stir at room temperature (about 32° C.). About two days later, another 5 mole percent of catalyst was added to the reaction mixture.

After about 2 more hours, 5 milliliters of water were added to the reaction mixture, and the phases were separated and concentrated using a rotary evaporator. The organic phase was concentrated to approximately 0.5 milliliters. The reaction mixture was purified by column chromatography. 124 grams of product was collected for a yield of 41%. Infrared Spectroscopy, Proton Nuclear Magnetic Resonance ($^1$H NMR), and $^{13}$C Attached Proton Test confirmed the structure of the product as isopropyl-2-(4-methoxy-phenyl)-4,5-dihydro-thiazole-4-benzyl-4-carboxylate (C).

EXAMPLE 4

6 grams of isopropyl-2-(4-methoxy-phenyl)-4,5-dihydro-thiazole-4-benzyl-4-carboxylate (C) was produced as in Example 3 and dissolved in 10 milliliters trichloromethane. The solution was placed in a 10 cm polarimetry tube and the optical activity of the solution was measured using a polarimeter. Optical activity were taken in each run and the average was recorded as α, observed rotation. Table 1 shows the average observed rotation for each of three runs.

TABLE 1

Observed Rotation

| Experiment | Average Observed Rotation (°) |
|---|---|
| 1 | −0.022 |
| 2 | −0.019 |
| 3 | −0.017 |
| Overall Average | −0.0193 |

The rotation of trichloromethane was +0.004 degrees. The overall average observed rotation corresponds to a specific rotation, $[\alpha]_D^{20}$, of −32.2 (degrees)(mL)/(dm)(g).

Given that the purified compound is optically active and that none of the asymmetric catalyst was observed in the Proton Nuclear Magnetic Resonance ($^1$H NMR), and $^{13}$C Attached Proton Test of Example 3, it can be assumed that the benzylation of 2-(4-methoxy-phenyl)-4,5-dihydro-thiazole-4-carboxylic acid isopropyl ester (A) occurred in an enantioselective fashion and that the product produced is the (−)-enantiomer.

EXAMPLE 5

All compounds were used without further purification. The surfactants Rhodafac RE 610 and Soprophor FL were obtained from Rhône-Poulenc, Surfynol 465 from Air Products, Synperonic NP 10 from ICI and sodium lauryl sulfate from Fluka. For agitation a shaking machine was used (Buhler KL Tuttlingen). Purities of the resulting crystals were measured by using a PolarMonitor polarimeter (IBZ Hannover). Ethanol was used as the solvent. The total crystal quantity was dissolved in a 1 mL cell at 20° C.)

45 mg of (R,R)—and (S,S)—amino acid derivatives were dissolved in 1 ml of a mixture of 20% v/v 2-hexanol, 12% v/v Rhodafac RE 610, 6% v/v Soprophor FL and 62% v/v water by heating to 80° C. in a 5 mL vial. After the organic derivative was completely dissolved the microemulsion was cooled down to room temperature and agitated using a shaking machine (420 rpm). During two hours no spontaneous crystallization was observed. The mixture was then seeded with two drops of a dilute, finely ground suspension of pure (S,S)—(−) amino acid or its ester crystals grown under similar conditions. After 2 hours of agitation the resulting crystals were filtered off, washed with water and dried in a gentle nitrogen stream.

EXAMPLE 6

35 mg of R- and S-4,5-dihydro-2-(2,4-dihydroxyphenyl)-4-methylthiazole-4-carboxylic acid were dissolved in 1 ml of a mixture of 9% N-methyl-pyrrolidone, 9% v/v 2-hexanol, 10% v/v Rhodafac RE 610, 5% v/v Soprophor FL and 68% v/v water by heating to 50° C. in a 5 mL vial. After the product was completely dissolved, the microemulsion was cooled down to room temperature and agitated with a shaking machine (350 rpm). During two hours, no spontaneous crystallisation was observed. The mixture was then seeded with two drops of a dilute, finely ground suspension of pure S-product crystals grown under similar conditions. After two hours of shaking, the resulting crystals were filtered off, washed with water and dried in a gentle nitrogen stream. The procedure yielded 5.4 mg (15.4%) of colorless crystals, with a greater than 90% purity of the S enantiomer.

EXAMPLE 7

2,4-Dibenzyloxybenzonitrile (0.121 mol) was dissolved in 5.85 g (0.127 mol) ethanol and 19.4 ml 1,2-dimethoxyethane in a double walled reactor. This solution was cooled to −5° C., stirred and saturated with dry HCl gas over 5 hours at 0-3° C. The reaction mixture was stirred overnight at 2-4° C. under nitrogen. During this time, a product crystallized. The white crystals were filtered off, washed with 1,2-dimethoxyethane (5° C., three times each with 13 ml) and dried. A total of 30 of the protected ethyl benzimidate was isolated (Yield 88.4%, purity 98.9%).

The protected ethyl benzimidate described above was dissolved in methanol to generate a 10% solution and was catalytically hydrogenated at room temperature using 5% Pd/C as a catalyst. The reaction was completed after 8 hours. The solution was filtered and the solvent evaporated to yield the deprotected product as an orange-yellow solid. The reaction yielded 19.6 g (94%) of product.

In contrast, the formation of the imidate with 2,4 dihydroxybenzonitrile was a low yielding process, generating the desired product in only 20% yield and with less than desired purity.

While this invention has been particularly shown and described with references to preferred embodiments thereof, it will be understood by those skilled in the art that various changes in form and details may be made therein without departing from the scope of the invention encompassed by the appended claims.

We claim:

1. A method of preparing an alkylated thiazoline carboxylic acid or a derivative thereof represented by Structural Formula (I):

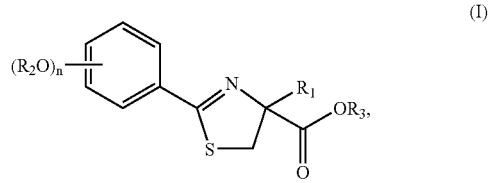

or a salt thereof,
wherein $R_1$ is a substituted or unsubstituted alkyl group;
each $R_2$ is, independently, —H or a substituted or unsubstituted alkyl group;
$R_3$ is —H, a substituted or unsubstituted alkyl group or a carboxyl protecting group; and
n is an integer from 1 to 5,
the method comprising:

(a) coupling a compound represented by Structural Formula (II):

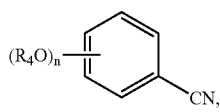
(II)

wherein each $R_4$ is, independently, a substituted or unsubstituted alkyl group
and n is an integer from 1 to 5,
with a cysteine ester represented by Structural Formula (III):

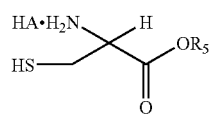
(III)

wherein A is an anion and $R_5$ is a substituted or unsubstituted alkyl group,
thereby forming a substituted thiazoline carboxylic acid ester represented by Structural Formula (IV):

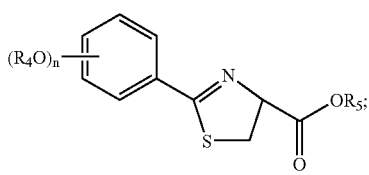
(IV)

(b) optionally, hydrolyzing the substituted thiazoline carboxylic acid ester to form a substituted thiazoline carboxylic acid represented by Structural Formula (V):

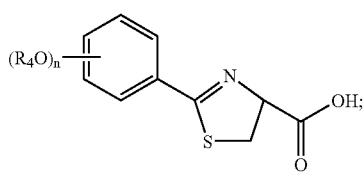
(V)

(c) optionally, protecting the carboxyl group of the substituted thiazoline carboxylic acid to form a protected thiazoline carboxylic acid represented by Structural Formula (VI):

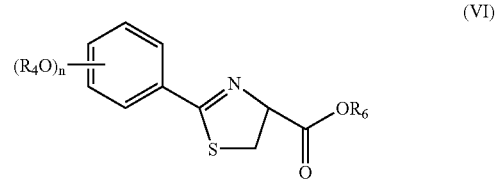
(VI)

wherein $R_6$ is a carboxyl protecting group;

(d) alkylating the optionally protected thiazoline carboxylic acid represented by Structural Formula (VII):

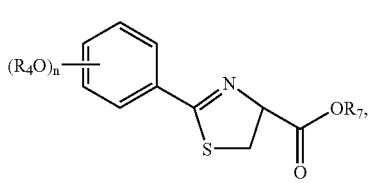
(VII)

wherein $R_4$ and n are as defined above and $R_7$ is —H, $R_5$ or $R_6$, with a compound having the formula $R_1$-L, wherein $R_1$ is defined as above and L is a leaving group, in the presence of a chiral phase transfer catalyst to produce an enantiomeric excess of either the (R)- or (S)-isomer of an alkylated optionally protected thiazoline carboxylic acid represented by Structural Formula (VIII):

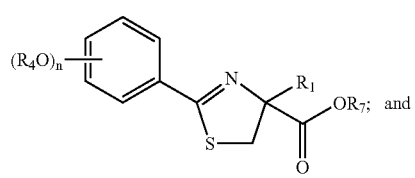
(VIII)

(e) optionally, hydrolyzing the optionally protected alkylated thiazoline carboxylic acid and cleaving ether groups,
thereby forming the compound represented by Structural Formula (I).

2. The method of claim 1 wherein $R_1$ is a substituted or unsubstituted C1 to C4 alkyl group.

3. The method of claim 1 wherein $R_1$ is substituted or unsubstituted methyl.

4. The method of claim 1 wherein each $R_2$ is a substituted or unsubstituted C1 to C4 alkyl group.

5. The method of claim 1 wherein $R_3$ is a substituted or unsubstituted C1 to C4 alkyl group or —H.

6. The method of claim 1 wherein $R_5$ is a substituted or unsubstituted C1 to C4 alkyl group.

7. The method of claim 1 wherein the cysteine ester of Method Step (a) is the (R) isomer.

8. The method of claim 1 wherein $R_7$ is an alkyl group.

9. The method of claim 1 wherein the phase transfer catalyst is represented by Structural Formula (IX):

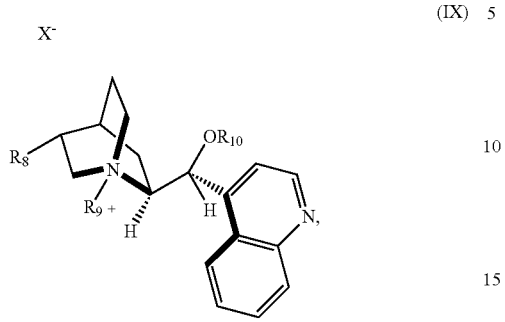
(IX)

or a salt thereof, wherein $R_8$ and $R_{10}$ are, independently, —H, a substituted or unsubstituted alkyl group, a substituted or unsubstituted aromatic group, or a substituted or unsubstituted heterocyclic group;

$R_9$ is a substituted or unsubstituted alkyl group, a substituted or unsubstituted aromatic group, or a substituted or unsubstituted heterocyclic group; and X is a halogen.

10. The method of claim 9 wherein $R_9$ is 9-anthracenylmethyl represented by Structural Formula (X):

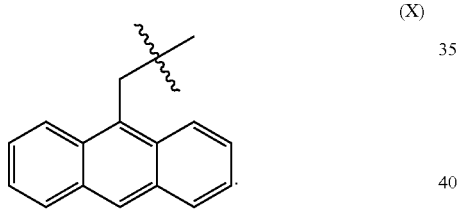
(X)

11. The method of claim 9 wherein $R_{10}$ is substituted or unsubstituted allyl.

12. The method of claim 9 wherein $R_8$ is substituted or unsubstituted ethenyl.

13. The method of claim 1 further comprising the step of further resolving the enantiomers of the compound represented by Structural Formula (I).

14. The method of claim 13 wherein the (S)-isomer of the compound represented by Structural Formula (I) is isolated from the enantiomers.

15. A method of preparing an alkylated thiazoline carboxylic acid represented by Structural Formula (XI):

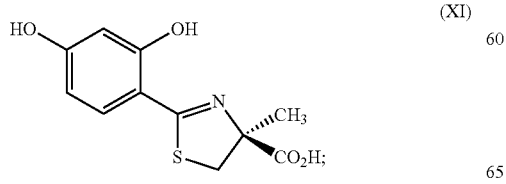
(XI)

or a salt thereof, the method comprising:

(a) coupling a compound represented by Structural Formula (XII):

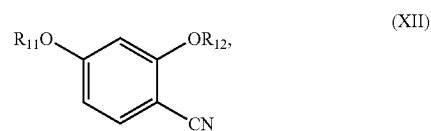
(XII)

wherein $R_{11}$ and $R_{12}$ are independently, a C1 to C4 substituted or unsubstituted alkyl group, with a cysteine ester represented by Structural Formula (XIII):

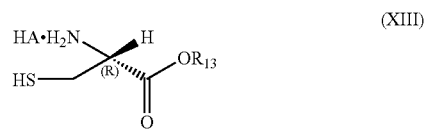
(XIII)

wherein A is an anion and $R_{13}$ is a substituted or unsubstituted alkyl group;

thereby forming a substituted thiazoline carboxylic acid ester represented by Structural Formula (XIV):

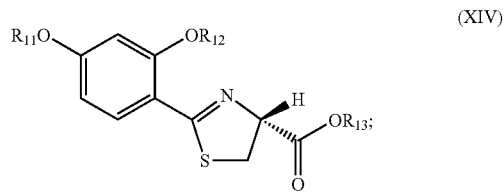
(XIV)

(b) optionally, hydrolyzing the substituted thiazoline carboxylic acid ester to form a substituted thiazoline carboxylic acid represented by Structural Formula (XV):

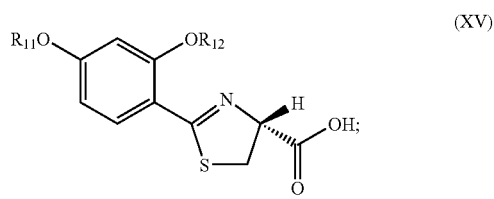
(XV)

(c) optionally, protecting the carboxyl group of the substituted thiazoline carboxylic acid to form a protected thiazoline carboxylic acid represented by Structural Formula (XVI):

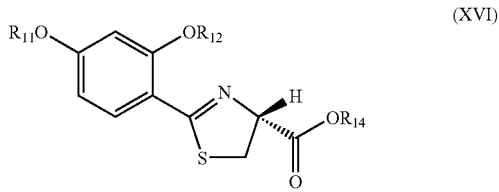
(XVI)

wherein $R_{14}$ is a carboxyl protecting group;

(d) alkylating the optionally protected thiazoline carboxylic acid represented by Structural Formula (XVII):

(XVII)
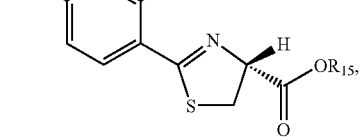

(XX)
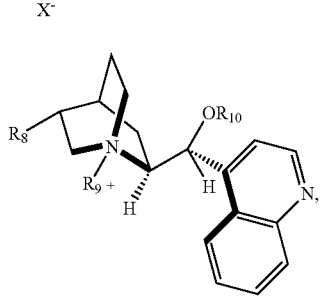

(f) optionally, purifying the (S)-isomer of the compound represented by Structural Formula (XX).

16. The method of claim 15, wherein $R_{11}$ and $R_{12}$ are each methyl groups.

17. The method of claim 15, wherein $R_{14}$ and $R_{15}$ are each iso-propyl.

18. The method of claim 15, wherein the phase transfer catalyst is represented by Structural Formula (IX):

(IX)
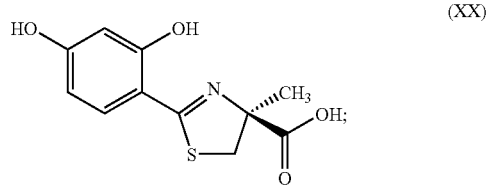

or a salt thereof, wherein $R_8$ and $R_{10}$ are, independently, —H, a substituted or unsubstituted wherein $R_{15}$ is H, $R_{13}$ or $R_{14}$, with a compound having the formula $CH_3$-L, wherein L is a leaving group, in the presence of a phase transfer catalyst thereby forming an alkylated protected thiazoline carboxylic acid represented by Structural Formula (XIX):

(XIX)
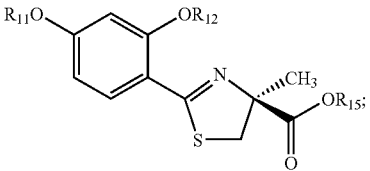

(e) hydrolyzing the protected alkylated thiazoline carboxylic acid and cleaving ether groups to form the compound represented by Structural Formula (XX):

alkyl group, a substituted or unsubstituted aromatic group, or a substituted or unsubstituted heterocyclic group;

$R_9$ is a substituted or unsubstituted alkyl group, a substituted or unsubstituted aromatic group, or a substituted or unsubstituted heterocyclic group; and X is a halogen.

19. The method of claim 18, wherein $R_9$ is 9-anthracenylmethyl represented by Structural Formula (X):

(X)
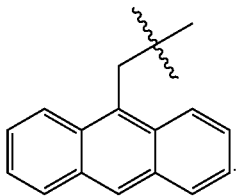

20. The method of claim 19, wherein $R_{10}$ is substituted or unsubstituted allyl and $R_8$ is substituted or unsubstituted ethenyl.

* * * * *